(12) United States Patent
Nakashima

(10) Patent No.: US 11,622,821 B2
(45) Date of Patent: Apr. 11, 2023

(54) MEDICAL MANIPULATOR

(71) Applicant: Olympus Corporation, Hachioji (JP)

(72) Inventor: Kohei Nakashima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/280,291

(22) Filed: Feb. 20, 2019

(65) Prior Publication Data

US 2019/0175292 A1 Jun. 13, 2019

Related U.S. Application Data

(63) Continuation of application No. PCT/JP2017/003906, filed on Feb. 3, 2017.

(51) Int. Cl.
*A61B 34/30* (2016.01)
*B25J 18/00* (2006.01)
(Continued)

(52) U.S. Cl.
CPC ............... *A61B 34/30* (2016.02); *B25J 9/126* (2013.01); *B25J 9/1633* (2013.01); *B25J 18/00* (2013.01);
(Continued)

(58) Field of Classification Search
CPC ... A61B 34/30; A61B 2090/031; B25J 9/1633
See application file for complete search history.

(56) References Cited

U.S. PATENT DOCUMENTS

| 2004/0169484 A1* | 9/2004 | Iribe | B25J 9/1633 |
| | | | 318/434 |
| 2008/0046122 A1* | 2/2008 | Manzo | A61B 34/74 |
| | | | 700/245 |

(Continued)

FOREIGN PATENT DOCUMENTS

| JP | 8-224246 | 9/1996 |
| JP | 9-254079 | 9/1997 |

(Continued)

OTHER PUBLICATIONS

International Search Report and Written Opinion from corresponding International Application No. PCT/JP2017/003906, dated Mar. 21, 2017.

*Primary Examiner* — Rex R Holmes
*Assistant Examiner* — Jennifer L Ghand
(74) *Attorney, Agent, or Firm* — Scully, Scott, Murphy & Presser, P.C.

(57) ABSTRACT

Embodiments of the technology disclosed herein is directed to a medical manipulator capable of detecting an instant when a tip of the medical manipulator is unexpectedly separated from a body tissue and thus avoid making contact with surrounding body tissues. The technology disclosed eliminates the needs for providing a force sensor located on the tip of the medical manipulator. The medical manipulator includes a movable unit at one end and an electric motor, a control unit, and an operation input unit at opposed end thereof. The movable unit includes a treating unit for treating the body tissue. The electric motor is configured to operate the movable unit. The electric motor includes a current sensor or a torque detecting unit for detecting the torque of the motor. The control unit includes a torque reducing unit for reducing the torque transmitted to the movable unit from the electric motor.

12 Claims, 7 Drawing Sheets

(51) Int. Cl.
*B25J 9/16* (2006.01)
*B25J 9/12* (2006.01)
*B25J 19/06* (2006.01)
*A61B 90/00* (2016.01)

(52) U.S. Cl.
CPC ......... *B25J 19/06* (2013.01); *A61B 2090/031* (2016.02); *A61B 2090/066* (2016.02)

(56) References Cited

U.S. PATENT DOCUMENTS

| | | | |
|---|---|---|---|
| 2009/0062813 A1* | 3/2009 | Prisco | A61B 34/37 606/130 |
| 2014/0081460 A1* | 3/2014 | Ando | B25J 9/1641 700/260 |
| 2016/0089790 A1* | 3/2016 | Wang | B25J 9/1676 700/255 |
| 2017/0007336 A1* | 1/2017 | Tsuboi | B25J 9/06 |
| 2017/0189130 A1* | 7/2017 | Weir | A61B 34/37 |
| 2018/0049816 A1* | 2/2018 | Shelton, IV | F16H 3/22 |
| 2018/0168747 A1* | 6/2018 | Kopp | H02K 11/20 |
| 2019/0038371 A1* | 2/2019 | Wixey | A61B 34/35 |

FOREIGN PATENT DOCUMENTS

| | | |
|---|---|---|
| JP | 2000-316872 | 11/2000 |
| JP | 2004-364396 | 12/2004 |
| JP | 2013-119133 | 6/2013 |
| JP | 2016-64474 | 4/2016 |

\* cited by examiner

MEDICAL MANIPULATOR

CROSS-REFERENCE TO RELATED APPLICATION

This application is a continuation application of PCT Application No. PCT/JP2017/003906 filed on Feb. 3, 2017, which is hereby incorporated by reference in its entirety.

TECHNICAL FIELD

The disclosed technology relates generally to manipulators and more particularly, to a medical manipulator used in treating a body tissue.

DESCRIPTION OF THE RELATED ART

There is a conventional control device that prevents damage to a robot arm and a target object caused by an increase in torque when the robot arm comes into contact with the target object. The robot arm detects the contact through a comparison of the same state quantities of an actual machine unit including an electric motor, a motor control unit, a mechanical unit, and a simulation unit that simulates these units as disclosed in Japanese Patent Application Publication No. 2004-364396. Furthermore, there is also a known robot arm that uses a force sensor to detect contact of an elastic end effector and that corrects controlled variables so that the end effector does not deform as disclosed in Japanese Patent Application Publication No. 2013-119133.

However, bringing a manipulator into contact with a body tissue that is defines as a target object, and then applying force, will deform the body tissue. Therefore, if the manipulator is unexpectedly separated from the body tissue in a state where the manipulator is grabbing the body tissue and applying pressure, there is a risk that the manipulator will displace rapidly and thus come into contact with body tissue in the surrounding area.

While the control device in Japanese Patent Application Publication No. 2004-364396 and the robot arm in Japanese Patent Application Publication No. 2013-119133 are able to detect the instant that a robot arm comes into contact with a target object, it is difficult for control device and the robot arm to detect an instant that the robot arm is unexpectedly separated from the target object. Because manipulators for performing treatments on body tissue are extremely small, it is particularly difficult to provide force sensors at every joint thereof, as disclosed in Japanese Patent Application Publication No. 2013-119133.

Accordingly, there is a need for a medical manipulator that can effectively overcome the drawbacks of the aforementioned devices.

BRIEF SUMMARY OF EMBODIMENTS

Embodiments of the technology disclosed herein is directed to a medical manipulator capable of detecting an instant when a tip of the medical manipulator is unexpectedly separated from a body tissue and thus avoid making contact with surrounding body tissue. The technology disclosed herein eliminates the needs for providing a force sensor located on the tip of the medical manipulator.

According to the embodiment of the technology disclosed herein, a medical manipulator comprises a movable unit at one end and a combination of an electric motor, a control unit, and an operation input unit at opposed end thereof. The movable unit includes a treating unit at a tip thereof for treating a body tissue. The electric motor is configured to operate the movable unit. The electric motor includes a current sensor or a torque detecting unit for detecting the torque of the motor. The control unit includes a torque reducing unit for reducing the torque transmitted to the movable unit from the electric motor when a reduction in an absolute value of the torque per unit time detected by the torque detecting unit is equal to or greater than a specified second threshold in a state where the absolute value of the torque has been continuously equal to or greater than a specified first threshold for a specified or longer period of time.

According to this embodiment, when the movable unit treats the body tissue using the treating unit at the tip, the torque of the electric motor is detected by the torque detecting unit, and a determination is made as to whether the absolute value of the detected torque is equal to or greater than a specified first threshold. When the absolute value of the torque is equal to or greater than the first threshold, the value is monitored to determine whether or not this state continues for a specified or longer period of time. When this state continues for the specified or longer period of time, a determination is made as to whether the reduction of the absolute value of the torque per unit time is equal to or greater than a specified second threshold.

A state where the absolute value of the torque is equal to or greater than the first threshold is a state where a load is being applied to the movable unit, and setting the condition that the state continues for a specified or longer period of time excludes cases where the load is applied due to acceleration or deceleration. In this manner, it is possible to discern a state where a load is being applied to the movable unit by something other than acceleration or deceleration, such as, for example, a state where the treating unit on the tip of the movable unit is pushing or pulling on the body tissue.

Furthermore, because a reduction in the absolute value of the torque per unit time that is equal to or exceeding the specified second threshold in this state means that the treating unit has unexpectedly separated from the body tissue, the abrupt displacement of the treating unit caused by a dislocation reaction is suppressed and contact with the surrounding tissue is avoided or prevented in this case by transmitting a reduction in torque from the electric motor to the movable unit through the torque reducing unit.

In the aforementioned state, the torque reducing unit may reduce the torque by operating the electric motor in an opposite direction. Therefore, when it is detected that the treating unit is unexpectedly separated from the body tissue in a state where torque is being generated in one direction by the electric motor, the torque being applied is eliminated instantly and the abrupt displacement of the treating unit caused by a dislocation reaction is suppressed, and making contact with surrounding tissue is avoided or prevented, by the torque reducing unit reversely operating the electric motor.

Moreover, in the embodiment described herein above, the torque reducing unit is provided with a storage unit for storing an angular position for the electric motor when the absolute value of the torque detected by the torque detecting unit is equal to the first threshold, and the torque is reduced by operating the electric motor toward the angular position stored in the storage unit. Therefore, the body tissue will begin to be pushed and pulled by the treating unit at or above a prescribed degree of force when the absolute value of the torque detected by the torque detecting unit is equal to the first threshold. Accordingly, the angular position of the electric motor at this time is stored in the storage unit, and, by operating the electric motor toward the angular position stored in the storage unit when it is detected that the treating unit unexpectedly separated from the living tissue, the torque reducing unit is restored to the point where the pushing and pulling began, and the abrupt displacement of the treating unit caused by the dislocation reaction of the treating unit from the body tissue is suppressed, thus avoiding or preventing making any contact with the surrounding tissue.

Furthermore, a clutch capable of intermittently transmitting the torque of the electric motor to the movable unit is positioned between the electric motor and the movable unit, and the torque reducing unit may reduce the torque by cutting off the clutch. Therefore, because the torque reducing unit cuts off the clutch and reduces the torque transmitted to the movable unit when it is detected that the treating unit unexpectedly is separated from the body tissue, and the abrupt displacement of the treating unit caused by the dislocation reaction of the treating unit from the body tissue is suppressed, and thus avoiding or preventing making contact with the surrounding tissue.

Furthermore, the movable unit is provided with a plurality of links and at least one joint that connects the links to one another and is driven by the electric motor, where the joint may be provided with a damper for generating damping force proportional to the rotational speed of the joint. Therefore, from the time the torque detecting unit detects that the treating unit has separated from the body tissue to the instant or time that the torque reducing unit implements torque reduction, rapid rotation of the joint is suppressed by the damper, which thus more reliably suppresses the abrupt dislocation of the treating unit.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

Figure 1:
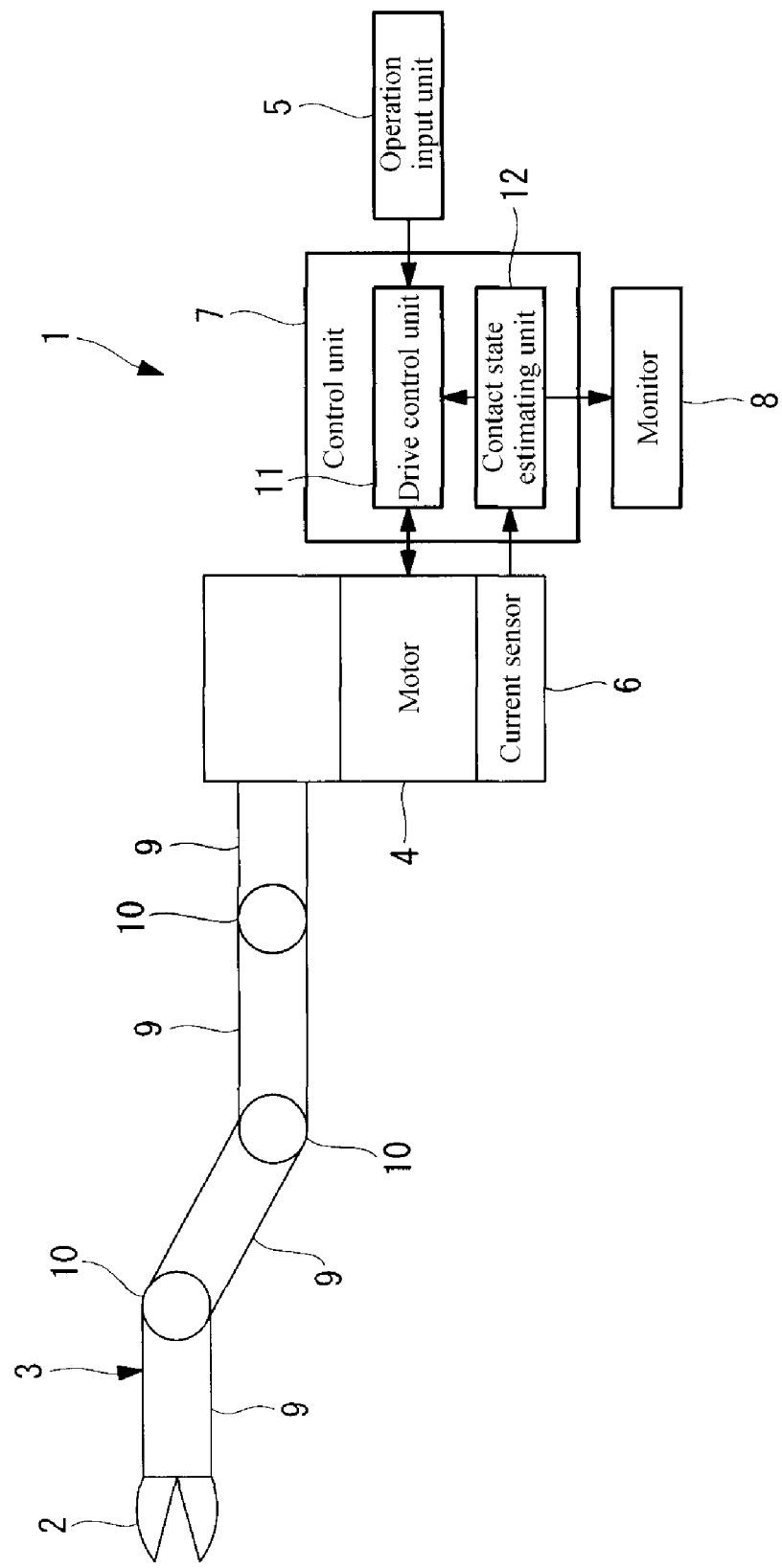
FIG. 1 is a schematic diagram illustrating a medical manipulator according to an embodiment of the present invention.

As illustrated in FIG. 1, the medical manipulator 1 comprises a movable unit 3 at one end and a combination of an electric motor 4, a control unit 7, and an operation input unit 5 at opposed end thereof according to one of the embodiments disclosed herein. The movable unit 3 has a tip or a distal end defined by a treating unit 2 for treating a body tissue or the likes (not shown in FIG. 1). The electric motor 4 is used to operate the movable unit 3. The electric motor includes a current sensor (torque detecting unit) 6 for detecting a current value of the electric motor 4. A control unit (torque reducing unit) 7 is used to control the electric motor 4 in accordance with the current value detected by input into the operation input unit 5 and the current sensor 6. The operation input unit 5 is operated by an operator or a user, using a monitor 8 for displaying the state of contact of the treating unit 2 with respect to the body tissue.

In the example illustrated in FIG. 1, the movable unit 3 is an articulated unit having a plurality of links 9 and a joint 10 is used for coupling the links 9 to one another in a relatively rotatable manner. The electric motor 4 is used for each of the joints 10 and is made to transmit motive force to each of the joints 10 through a power transmission member, such as a wire, and the like. To simplify the illustration, only one of the electric motors 4 is illustrated in FIG. 1. The current sensor 6 is provided for each of the electric motors 4, and is made to detect the current value flowing to each of the electric motors 4. The control unit 7 is provided with a drive control unit 11 for calculating a drive command and outputting the command to the electric motor 4, and a contact state estimating unit 12 for estimating the state of contact between the treating unit 2 and the body tissue based on the current value of each of the electric motors 4 detected by the current sensor 6.

The drive control unit 11 calculates a command signal and outputs the signal to each of the electric motors 4 so as to operate each of the joints 10 of the movable unit 3 based on input from an operator to the operation input unit 5. Thus, when the contact state estimating unit 12 satisfies a predetermined condition, the drive control unit 11 outputs a command signal to the electric motor 4 for operating each of the joints 10 so as to prevent abrupt displacement of the movable unit 3.

Figure 2:
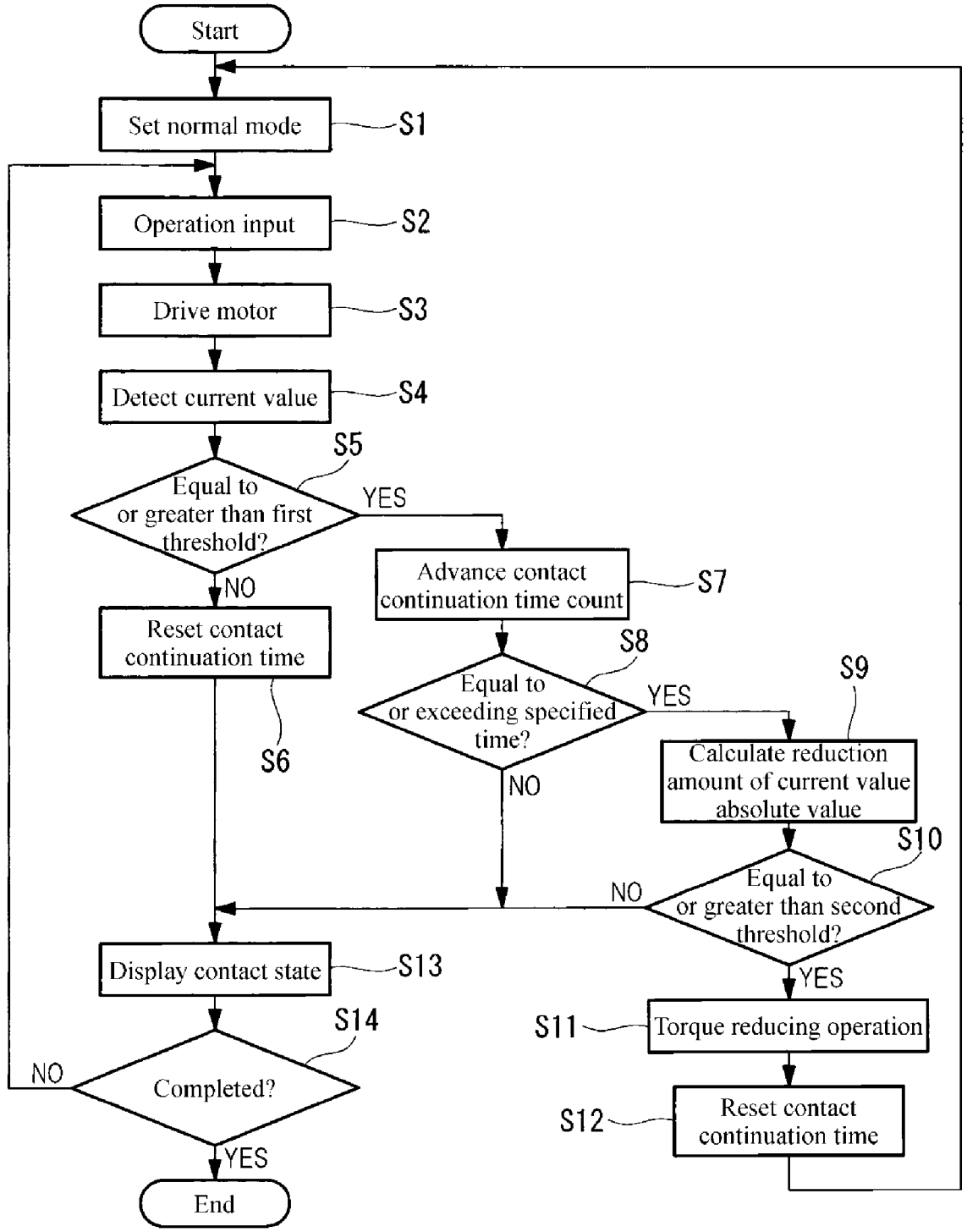
FIG. 2 is a flow chart for describing the operation of the medical manipulator of FIG. 1.

Specifically, as illustrated in FIG. 2, when control operation starts in the present embodiment, the drive control unit 11 sets a normal mode for driving the movable unit 3 in accordance with an operation input in step S1, When an operator performs operation input from the operation input unit 5 in step S2, a drive command is calculated and then output to each of the electric motors 4 by the drive control unit 11, and each of the electric motors 4 is driven by the command in step S3.

When the electric motor 4 is operating, a current value is detected by the current sensor 6 as denoted in step S4, and the contact state estimating unit 12 determines whether the absolute value of the current value of each of the electric motors 4 is at or above the first threshold as noted in step S5. And when the absolute value is smaller than a first threshold (first state), resets a contact continuation time to be described later in step S6. When the absolute value is at or above the first threshold (second state), it is assumed that the treating unit 2 and the body tissue are making contact at a specified load, the count for the contact continuation time showing how long this state continued is advanced as noted in step S7, and then a determination is made as to whether the contact continuation time is or exceeds a specified time Δt at step S8. When the contact continuation time is shorter than the specified time Δt, it is determined that either a load was applied temporarily due to acceleration or deceleration for operating the movable unit 3, or that the operating direction of the movable unit 3 was switched by an operator. On the other hand, when the contact continuation time is or exceeds the specified time Δt (third state), it is determined that contact by the treating unit 2 with the body tissue in accordance with a specified load is taking place in a continuous manner. For example, when the treating unit 2 is a pair of grasping forceps, the operation is that the grasping forceps holding the body tissue and then pulling the body tissue in one direction. Therefore, when the medical manipulator 1 is in this contact state (third state), the contact state estimating unit 12 calculates the reduction of the absolute value of the current per unit time value detected by the current sensor 6 in step S9, and determines whether the reduction amount is equal to or greater than a specified second threshold in step S10. When the reduction is by means of a reduction amount that is equal to or greater than the second threshold, the contact state estimating unit 12 outputs this fact to the drive control unit 11, and the drive control unit 11 drives the electric motor 4 in a torque reducing mode at step S11.

The torque reducing mode through the drive control unit 11 in the present embodiment is an operating mode for reversely operating the electric motor 4 by exactly a specified angle. After the electric motor 4 has been driven in the torque reducing mode, the contact continuation time is reset in step S12. After the contact continuation time has been reset, the process repeats from step S1.

The contact state is displayed on the monitor 8 in step S13 in which the contact state is estimated by the contact state estimating unit 12 in a first state, a second state, and/or a third state.

The first state is the state when it is determined in step S5 that the absolute value of the current value of the electric motor 4 is smaller than the first threshold.

The second sate is the state when it is determined in step S8 that the time period during which the absolute value of the current value of the electric motor 4 was equal to or greater than the first threshold is shorter than the specified time Δt.

The third state is the state when it is determined in step S10 that the reduction of the absolute value of the current per unit time of the electric motor 4 is smaller than the second threshold.

Following the step S13, if the treatment continues in step S14, the process repeats from step S2.

The operation of the medical manipulator 1 according to the present embodiment configured in this way will be described hereinafter.

To treat a body tissue using the medical manipulator 1 according to the present embodiment, a user or an operator, after setting an operation mode to a normal mode in step S1, operates the operation input unit 5 in step S2, and the electric motor 4 is driven and operated by exactly a rotation angle corresponding to an input through the drive control unit 11 in step S3. At this time, the current value of each of the electric motors 4 is detected by the current sensor 6 in step S4.

Figure 3:
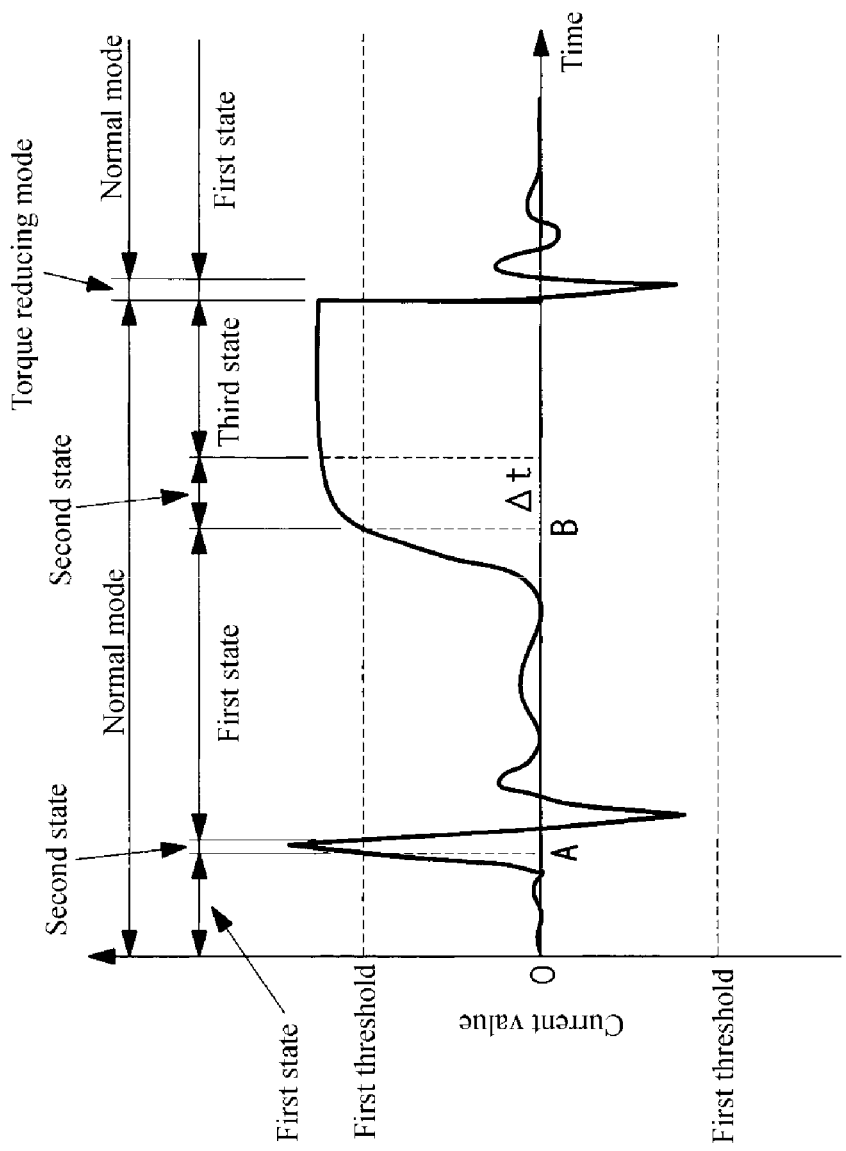
FIG. 3 is a graph illustrating an example of a current waveform, an operating mode, and a state of contact of an electric motor operated within the medical manipulator of FIG. 1.

When the current value of each of the electric motors 4 is detected, the detected current value is sent to the contact state estimating unit 12, and it is determined whether the absolute value of the detected current value is equal to or greater than the specified first threshold in step S5. When the current value changes as illustrated in FIG. 3, it is determined that the current values at time A and B are in the second state and equal to or greater than the first threshold.

When it is determined in step S5 that the absolute value of the current value is smaller than the first threshold, the contact continuation time is reset in step S6, the fact that the contact state is in the first state is displayed on the monitor 8 in step S13, then the process repeats from step S2.

When it is determined in step S5 that the absolute value of the current value is equal to or greater than the first threshold, the contact continuation time is advanced in step S7, and then a determination is made as to whether the contact continuation time is or exceeds a specified time Δt in step S8.

Figure 4:
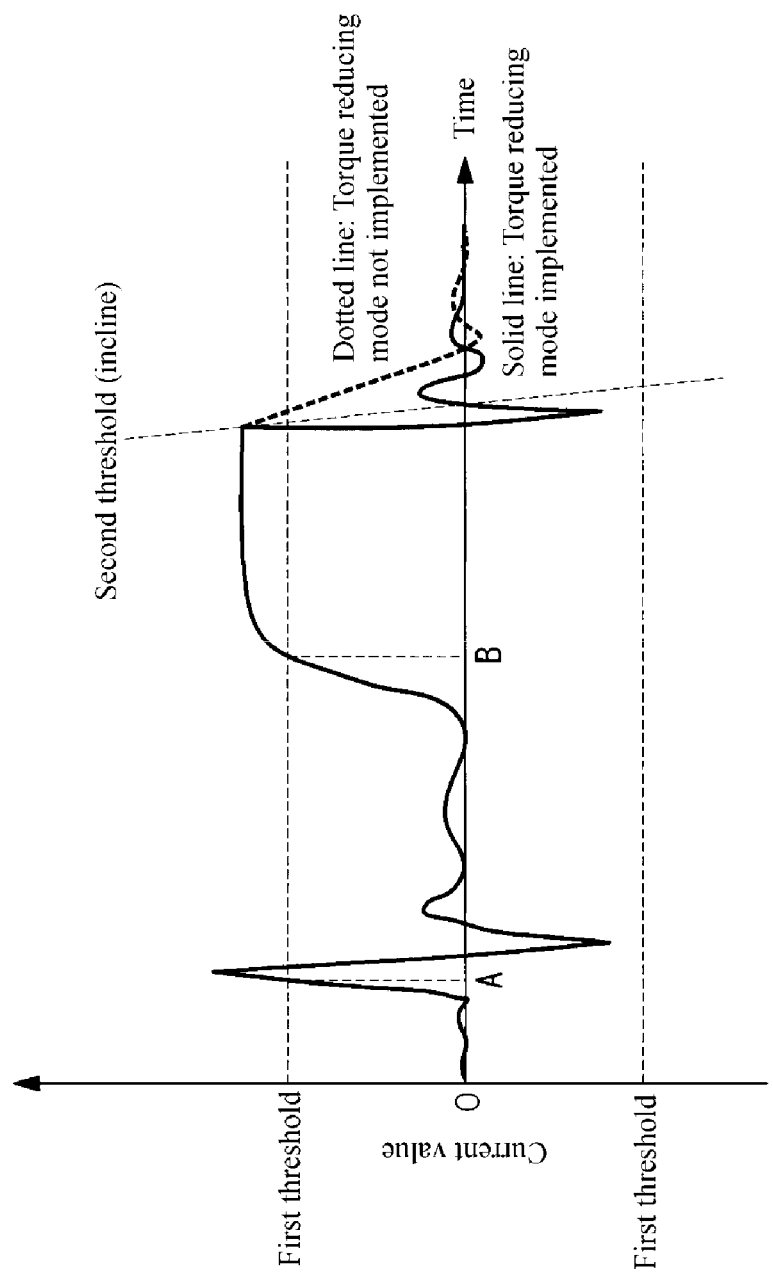
FIG. 4 is a graph illustrating the presence or absence of the implementation of a torque reducing mode in the current waveform of the motor provided in the medical manipulator in FIG. 1.

When the contact continuation time is shorter than the specified time Δt, the fact that the contact state in the second state is displayed on the monitor 8 in step S13, then the process repeats from step S2. On the other hand, when the contact continuation time is or exceeds the specified time Δt, the reduction amount of the absolute value of the current value is calculated in step S9, and is monitored to see whether a change has occurred such that a per time unit reduction is equal to or greater than the second threshold in step S10 as illustrated in FIG. 4.

Assume the situation A is that the absolute value of the current value that has been continuously equal to or greater than the first threshold for at least the specified time Δt.

Also, assume the situation B is that the reduction in the absolute value of the current value per unit time is equal to or greater than the second threshold.

When a current value change occurs with combination of situation A and situation B, it is possible that the treating unit 2 is unexpectedly separated from the living tissue in a state where the living tissue is being pushed and pulled by the treating unit 2.

Therefore, the electric motor 4 is operated by the drive control unit 11 using the torque reducing mode in step S11.

Furthermore, after the motor 4 is driven exactly a specified angle by the torque reducing mode, the contact continuation time is reset in step S12, and the process repeats from step S1.

When the reduction in the absolute value of the current per unit time is smaller than the second threshold when a state where the absolute value of the current value has been continuously equal to or greater than the first threshold for at least the specified time Δt, the fact that the contact state is in the third state is displayed on the monitor 8 in step S13, and the process repeats from step S2.

According to the present embodiment, unexpected separations of the treating unit 2 from the body tissue can be detected quickly by monitoring the current value of the electric motor 4. Accordingly, the movable unit 3 is made small because there is no need to add or provide a force sensor on the tip thereof. Furthermore, the electric motor 4 is operated in a reverse direction exactly a specified angle when it is detected that the treating unit 2 has unexpectedly separated from the body tissue, which then provides an advantage in that the torque of the electric motor 4 immediately drops, which allows suppression of the abrupt displacement of the treating unit 2 caused by the dislocation reaction of the treating unit 2 from the body tissue, and to thus avoid making contact with the surrounding body tissues.

Furthermore, because a state where the absolute value of the current value has been continuously equal to or greater than the first threshold for at least the specified time Δt is an example of one condition for driving the electric motor 4 using the torque reducing mode, operation is performed smoothly without the torque dropping due to large changes in the current value brought on by the switching of the operating direction of the treating unit 2 due to acceleration, deceleration, or operation.

Moreover, according to the present embodiment, the contact state estimated by the contact state estimating unit 12 is displayed on the monitor 8, which is an advantage because the user or operator is able to adjust the contact state themselves, and because the frequency with which the treating unit 2 unexpectedly separates from the body tissue is therefore reduced.

Figure 5:
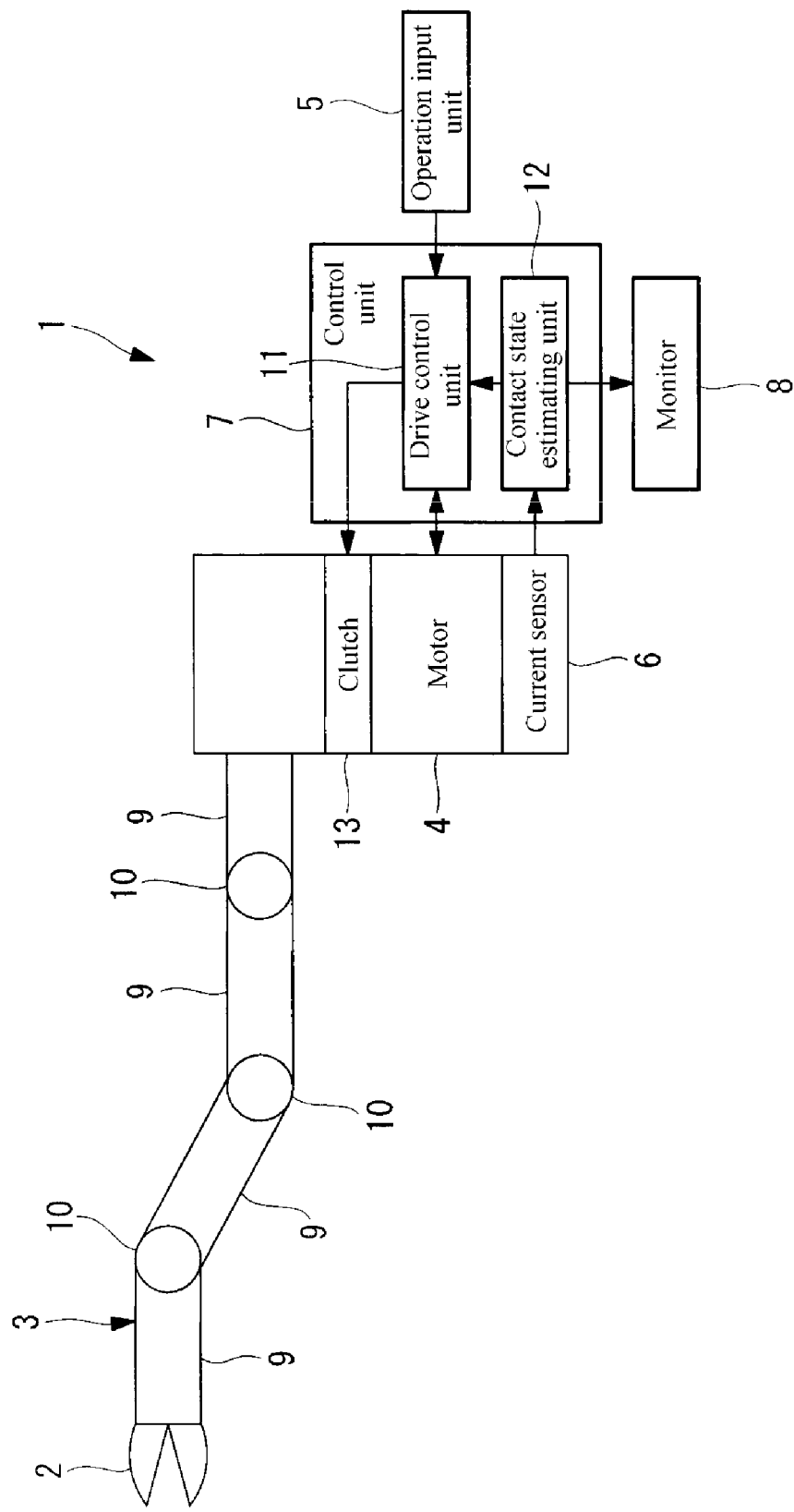
FIG. 5 is a schematic diagram illustrating a first embodiment of the medical manipulator in FIG. 1.

Note that while the control unit 7 for controlling the electric motor 4 was exemplified as a torque reducing unit for reducing torque transmitted to the movable unit 3 from the electric motor 4 when the treating unit 2 is separated from the body tissue, a torque reducing unit provided with the clutch 13, is arranged between the electric motor 4 and the movable unit 3, the contact state estimating unit 12, and the drive control unit 11, illustrated in FIG. 5, as the second embodiment. Therefore, by cutting off the clutch 13 when a current value change where the reduction in the absolute value of the current per unit time is equal to or greater than the second threshold in a state where the absolute value of the current value has been continuously equal to or greater than the first threshold for the specified time Δt or longer, the torque transmitted to the movable unit 3 from the electric motor 4 can be reduced, abrupt displacement of the treating unit 2 caused by the treating unit 2 being separated from the body tissue can be suppressed, and contact with the surrounding tissue can be avoided. In this case, the clutch 13 may be connected after having been cut off for a short time.

Figure 6:
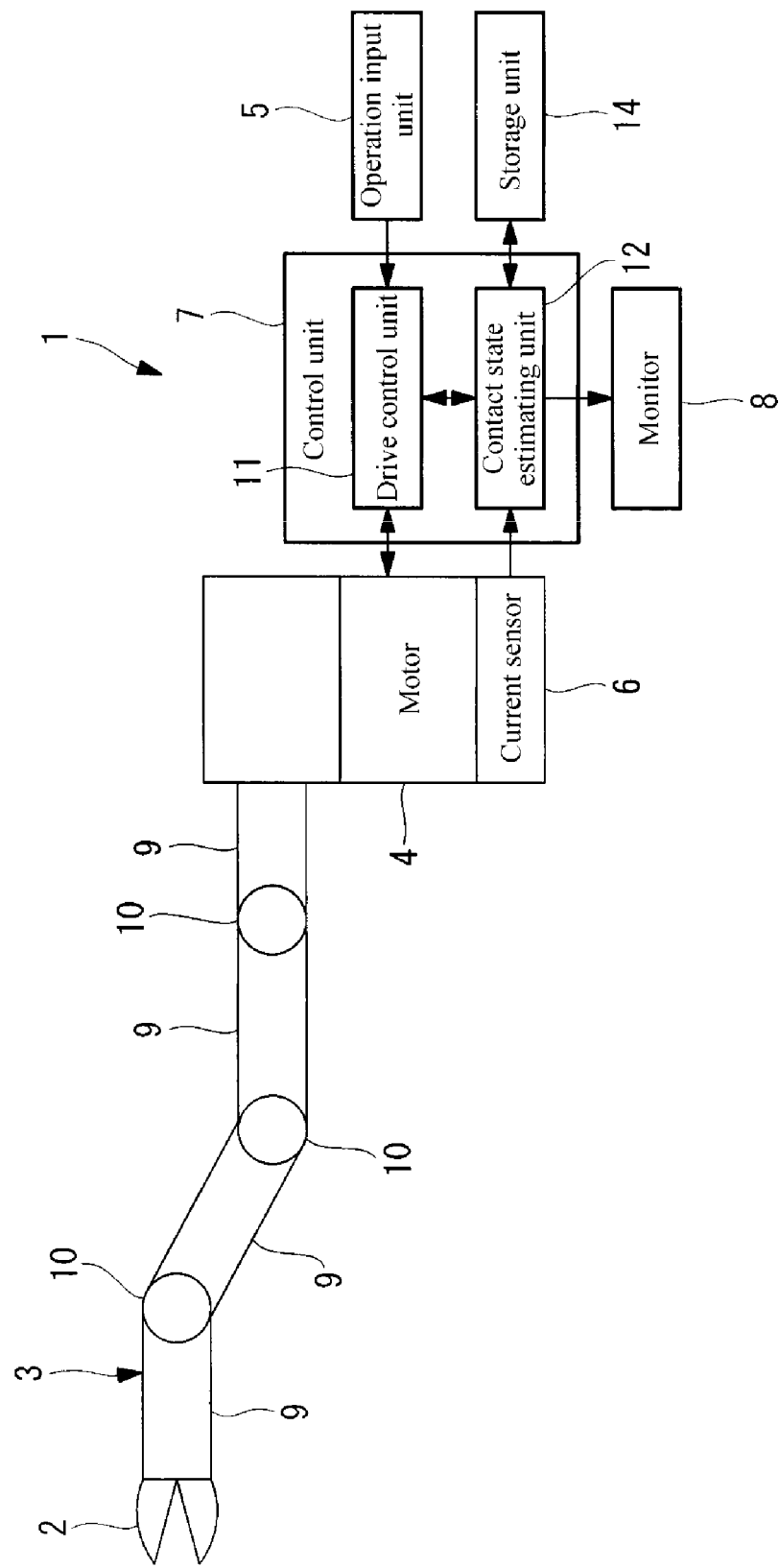
FIG. 6 is a schematic diagram illustrating a second embodiment of the medical manipulator in FIG. 1.

Moreover, a storage unit 14 is provided in the third embodiment as illustrated in FIG. 6 for storing the angular position of each electric motor 4 at the point in time when the absolute value of the current value exceeded the first threshold, and the drive control unit 11 is made to operate the electric motor 4 toward the angular position stored in the storage unit 14 when it is detected that the treating unit 2 has unexpectedly separated from the living tissue. This also allows the movable unit 3 to be restored to a state where a load of a specific size was just beginning to be applied, and the torque transmitted to the movable unit 3 from the electric motor 4 to be reduced.

Figure 7:
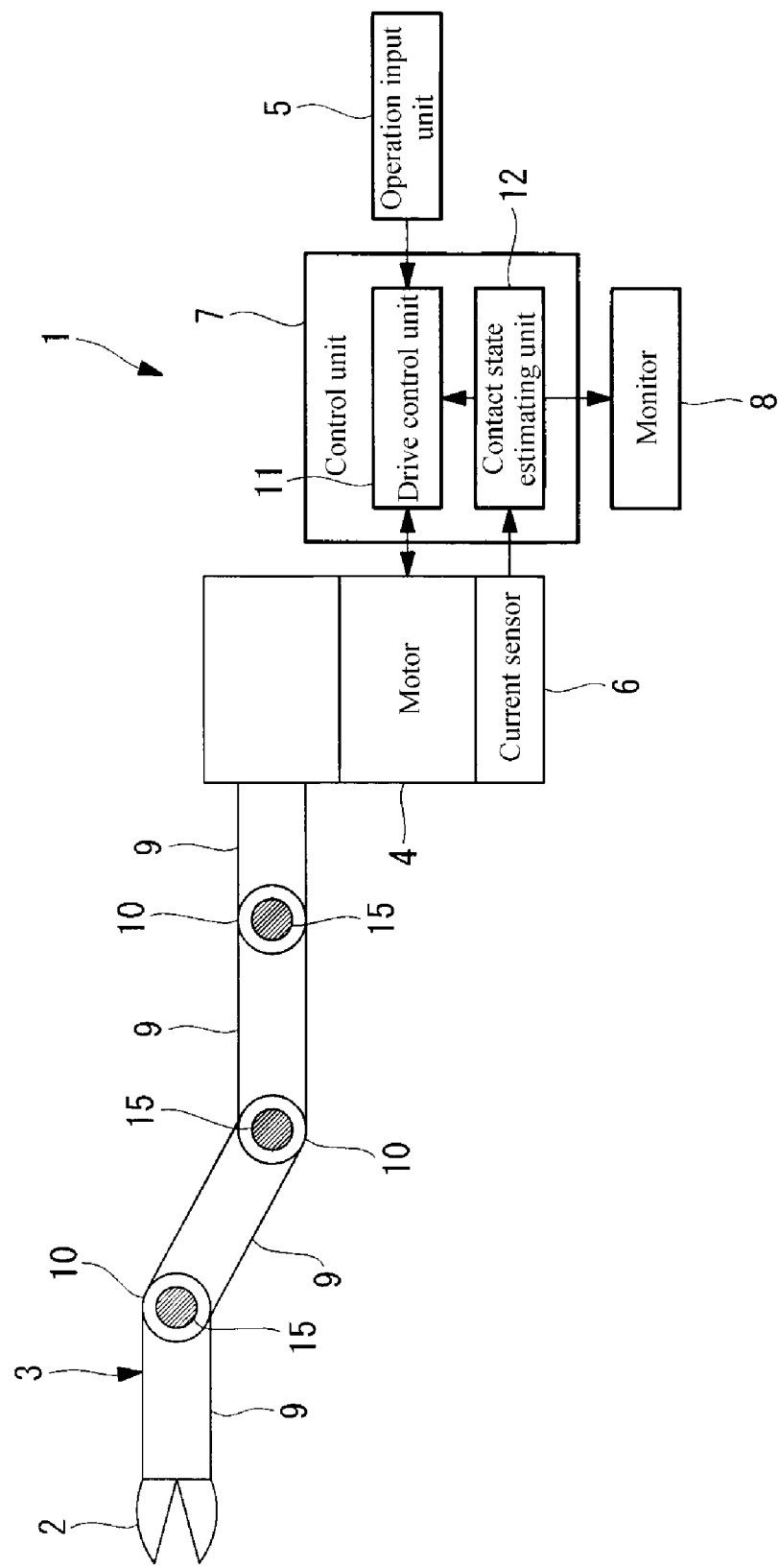
FIG. 7 is an overall configuration drawing illustrating a third embodiment of the medical manipulator in FIG. 1.

Furthermore, when a multi-jointed type movable unit 3 having a plurality of the links 9 and joints 10 is used as the movable unit 3, as illustrated in FIG. 7, a damper 15 that generates a damping force proportional to the rotational speed of the joint 10 can be provided on each of the joints 10. This configuration provides an advantage where abrupt displacement of each of the joints 10 is prevented even when there is a time lag from when it is detected through the current value of the electric motor 4 that the treating unit 2 unexpectedly separated from the body tissue to when the torque reducing mode operates. Any damper using a method having a damping coefficient that does not interfere with the operation of the movable unit 3 at the low speeds required for treatment and that can prevent abrupt displacement at high speeds may be used as the damper 15. Moreover, while torque was estimated in the third embodiment by detecting the current value of the electric motor 4, torque may be detected directly without using the current value, while other state quantities enabling the calculation of torque may also be used.

In sum, embodiments of the technology disclosed herein is directed to a medical manipulator capable of detecting the instant when a tip or a distal end of the medical manipulator is unexpectedly separated from a body tissue and thus avoid making contact with surrounding body tissue. The technology disclosed herein eliminates the needs for providing a force sensor located on the tip of the medical manipulator. Although the medical manipulator is configured or constructed to be used in medical field such as body tissues, but one of ordinary skill in the art would appreciate that the embodiments of the technology disclosed herein is applicable to other technology or manufacturing fields depending on the specific configurations.

According to the various embodiments of the technology disclosed herein, a medical manipulator comprises a movable unit at one end and a combination of an electric motor, a control unit, and an operation input unit at opposed end thereof. The movable unit includes a treating unit at a tip thereof for treating a body tissue. The electric motor is configured to operate the movable unit. The electric motor includes a current sensor or a torque detecting unit for detecting the torque of the motor. The control unit includes a torque reducing unit for reducing the torque transmitted to the movable unit from the electric motor when a reduction in an absolute value of the torque per unit time detected by the torque detecting unit is equal to or greater than a specified second threshold in a state where the absolute value of the torque has been continuously equal to or greater than a specified first threshold for a specified or longer period of time.

According to this embodiment, when the movable unit treats the body tissue using the treating unit at the tip, the torque of the electric motor is detected by the torque detecting unit, and a determination is made as to whether the absolute value of the detected torque is equal to or greater than the specified first threshold. When the absolute value of the torque is equal to or greater than the first threshold, the value is monitored to determine whether or not this state continues for a specified or longer period of time. When this state continues for the specified or longer period of time, a determination is made as to whether the reduction of the absolute value of the torque per unit time is equal to or greater than the specified second threshold.

A state where the absolute value of the torque is equal to or greater than the first threshold is a state where a load is being applied to the movable unit, and setting the condition that the state continues for a specified or longer period of time excludes cases where the load is applied due to acceleration or deceleration. In this manner, it is possible to discern a state where a load is being applied to the movable unit by something other than acceleration or deceleration, such as, for example, a state where the treating unit on the tip of the movable unit is pushing or pulling on the body tissue.

Furthermore, because a reduction in the absolute value of the torque per unit time that is equal to or exceeding the specified second threshold in this state means that the treating unit has unexpectedly separated from the body tissue, the abrupt displacement of the treating unit caused by a dislocation reaction is suppressed and contact with the surrounding tissue is avoided or prevented in this case by transmitting a reduction in torque from the electric motor to the movable unit through the torque reducing unit.

In the aforementioned state, the torque reducing unit may reduce the torque by operating the electric motor in an opposite direction. Therefore, when it is detected that the treating unit is unexpectedly separated from the body tissue in a state where torque is being generated in one direction by the electric motor, the torque being applied is eliminated promptly and the abrupt displacement of the treating unit caused by a dislocation reaction is suppressed, and making contact with surrounding tissue is avoided or prevented, by the torque reducing unit reversely operating the electric motor.

Moreover, in the embodiment described hereinabove, the torque reducing unit is provided with a storage unit for storing an angular position for the electric motor when the absolute value of the torque detected by the torque detecting unit is equal to the first threshold, and the torque is reduced by operating the electric motor toward the angular position stored in the storage unit. Therefore, the body tissue will begin to be pushed and pulled by the treating unit at or above a prescribed degree of force when the absolute value of the torque detected by the torque detecting unit is equal to the first threshold. Accordingly, the angular position of the electric motor at this time is stored in the storage unit, and, by operating the electric motor toward the angular position stored in the storage unit when it is detected that the treating unit unexpectedly separated from the living tissue, the torque reducing unit is restored to the point where the pushing and pulling began, and the abrupt displacement of the treating unit caused by the dislocation reaction of the treating unit from the body tissue is suppressed, thus avoiding or preventing making any contact with the surrounding tissue.

Furthermore, a clutch capable of intermittently transmitting the torque of the electric motor to the movable unit is positioned between the electric motor and the movable unit, and the torque reducing unit may reduce the torque by cutting off the clutch. Therefore, because the torque reducing unit cuts off the clutch and reduces the torque transmitted to the movable unit when it is detected that the treating unit unexpectedly is separated from the body tissue, and the abrupt displacement of the treating unit caused by the dislocation reaction of the treating unit from the body tissue is suppressed, and thus avoiding or preventing making contact with the surrounding tissue.

Furthermore, the movable unit is provided with a plurality of links and at least one joint that connects the links to one another and is driven by the electric motor, where the joint may be provided with a damper for generating damping force proportional to the rotational speed of the joint. Therefore, from the time the torque detecting unit detects that the treating unit has separated from the body tissue to the instant or time that the torque reducing unit implements torque reduction, rapid rotation of the joint is suppressed by the damper, which thus more reliably suppresses the abrupt dislocation of the treating unit.

Finally, a method for controlling a manipulator that includes a movable part unit having a treating unit at a distal end for treating a body tissue. An electric motor is operating the movable unit. A torque detecting unit detecting a torque produced by the electric motor comprises the step of reducing the torque transmitted from the electric motor to the movable part when a reduction in an absolute value of the torque per unit time is equal to or is greater than a specified second threshold in a state where the absolute value of the torque detected by the torque detecting unit being continuously equal to or greater than a specified first threshold for a specified or longer period of time.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:
1. A medical manipulator comprising:
an electric motor configured to operate a movable unit comprising an end effector at a distal end for treating a body tissue;
a sensor configured to detect a torque produced by the electric motor; and a controller comprising hardware, the controller being configured to:
  determine whether a first condition that lasts longer than a specified time is present, the first condition being that an absolute value of the torque produced by the electric motor detected by the sensor is equal to or greater than a specified first threshold;
  in response to determining that the first condition that lasts longer than the specified time is present, determine whether a reduction of the absolute value of the torque occurs;
  in response to determining that the reduction of the absolute value of the torque occurs, determine whether an amount of the reduction of the absolute value of the torque per unit time is equal to or greater than a second threshold; and
  in response to determining that the amount of the reduction of the absolute value of the torque per unit time is equal to or greater than the second threshold, perform control to avoid the amount of the reduction of the absolute value of the torque per unit time from being equal to or greater than the second threshold.

2. The medical manipulator according to claim 1, wherein in performing control to avoid the amount of the reduction of the absolute value of the torque per unit time from being equal to or greater than the second threshold, the controller is configured to reduce the torque by operating the electric motor in an opposite direction.

3. The medical manipulator according to claim 1, wherein the controller is configured to:
  control a memory to store an angular position for the electric motor when the absolute value of the torque detected by the sensor is equal to the specified first threshold; and
  in performing control to avoid the amount of the reduction of the absolute value of the torque per unit time from being equal to or greater than the second threshold, reduce the torque by operating the electric motor toward the angular position stored in the memory.

4. The medical manipulator according to claim 1, further comprising a clutch configured to intermittently transmit the torque of the electric motor to the movable unit,
  wherein in performing control to avoid the amount of the reduction of the absolute value of the torque per unit time from being equal to or greater than the second threshold, the controller is configured to reduce the torque by cutting off the clutch.

5. The medical manipulator according to claim 1, further comprising the movable unit,
  wherein the movable unit comprises a plurality of links and at least one joint that connects the plurality of links to one another and is configured to be driven by the electric motor, and
  wherein the at least one joint comprises a damper configured to generate a damping force proportional to a rotational speed of the at least one joint.

6. The medical manipulator according to claim 5,
  wherein the at least one joint comprises a plurality of joints corresponding to the plurality of links connected to one another.

7. The medical manipulator of claim 1, further comprising the movable unit,
  wherein the end-effector is a grasping forceps.

8. The medical manipulator of claim 1, wherein the sensor is a current sensor.

9. A method for controlling a medical manipulator comprising a movable unit having an end-effector at a distal end for treating a body tissue, an electric motor configured to operate the movable unit, and a sensor configured to detect a torque produced by the electric motor, the method comprising:
  determining that a first condition lasts longer than a specified time, the first condition being that an absolute value of the torque produced by the electric motor detected by the sensor is equal to or greater than a specified first threshold;
  in response to determining that the first condition lasts longer than the specified time, determining that a reduction of the absolute value of the torque occurs;
  in response to determining that the reduction of the absolute value of the torque occurs, determining that an amount of the reduction of the absolute value of the torque per unit time is equal to or greater than a second threshold; and
in response to determining that the amount of the reduction of the absolute value of the torque per unit time is equal to or greater than the second threshold, performing control to avoid the amount of the reduction of the absolute value of the torque per unit time from being equal to or greater than the second threshold.

10. The method according to claim 9, comprising:
  in performing control to avoid the amount of the reduction of the absolute value of the torque per unit time from being equal to or greater than the second threshold, reducing the torque by operating the electric motor in an opposite direction.

11. The method according to claim 9, comprising:
  controlling a memory to store an angular position for the electric motor when the absolute value of the torque detected by the sensor is equal to the specified first threshold; and
  in performing control to avoid the amount of the reduction of the absolute value of the torque per unit time from being equal to or greater than the second threshold, reducing the torque by operating the electric motor toward the angular position stored in the memory.

12. The method according to claim 9,
  wherein the manipulator comprises a clutch disposed between the electric motor and the movable unit, the clutch being configured to intermittently transmit the torque of the electric motor to the movable unit, and
  wherein the method comprises, in performing control to avoid the amount of the reduction of the absolute value of the torque per unit time from being equal to or greater than the second threshold, reducing the torque by cutting off the clutch.

* * * * *